United States Patent [19]

Horzewski et al.

[11] Patent Number: 5,201,756
[45] Date of Patent: Apr. 13, 1993

[54] RADIALLY-EXPANDABLE TUBULAR ELEMENTS FOR USE IN THE CONSTRUCTION OF MEDICAL DEVICES

[75] Inventors: Michael J. Horzewski, San Jose; John W. Danforth, San Francisco; Jeff L. Kraus, San Jose; Hugh R. Sharkey, San Francisco, all of Calif.

[73] Assignee: Danforth Biomedical, Inc., Menlo Park, Calif.

[21] Appl. No.: 846,742

[22] Filed: Mar. 6, 1992

Related U.S. Application Data

[63] Continuation of Ser. No. 541,006, Jun. 20, 1990, abandoned.

[51] Int. Cl.⁵ .............................................. A61M 29/00
[52] U.S. Cl. .................................... 606/198; 604/104; 604/164; 604/264
[58] Field of Search ................. 606/198; 604/104, 158, 604/264, 53, 164, 171; 128/4, 6

[56] References Cited

U.S. PATENT DOCUMENTS

| 702,789 | 6/1902 | Gibson | 606/198 |
| 3,788,318 | 1/1974 | Kim et al. | 606/198 X |
| 3,789,852 | 2/1974 | Kim et al. | 606/198 X |
| 4,716,901 | 1/1988 | Jackson et al. | 606/198 X |
| 4,899,729 | 2/1990 | Gill et al. | 606/198 X |
| 4,921,479 | 5/1990 | Grayzel | 604/53 |

Primary Examiner—Michael H. Thaler
Attorney, Agent, or Firm—Townsend and Townsend

[57] ABSTRACT

A radially expandable intravascular medical device is disclosed. The device typically includes two members. The first member is an outer tube-shaped sheath which is radially expandable by being formed from elastic material or other means and having relatively low column strength. The second member is an inner portion extending throughout the outer tube. This inner portion includes a slit to allow it to expand radially as well. Using the structure diagnostic, therapeutic, or other desired objects may be conveyed through the device yet still enable the device to have a smaller cross-sectional area throughout most of its length than the object conveyed therethrough.

12 Claims, 7 Drawing Sheets

RADIALLY-EXPANDABLE TUBULAR ELEMENTS FOR USE IN THE CONSTRUCTION OF MEDICAL DEVICES

This is a Continuation of application Ser. No. 07/541,006 filed Jun. 6, 1990, now abandoned.

BACKGROUND OF THE INVENTION

This invention relates to medical devices and in particular to tubular medical devices or tubular components of medical devices that are used to convey diagnostic/therapeutic instruments into the confines of the human body. This invention further relates to tubular components or channels of medical devices that function to accommodate guidewires.

Tubular devices and tubular components of devices are often used in the practice of medicine to conduct or convey fluids, medications, blood products and/or diagnostic/therapeutic instruments into the confines of the human body. The use of these tubular structures enables: (1) the introduction of said items through the tissue planes of the body and (2) the delivery of said items to specific locations within the body. Our invention has particular application to the construction of tubular medical devices and tubular components of medical devices that are used to convey diagnostic/therapeutic instruments and/or guidewires into the human body.

A guiding catheter is an example of a tubular medical instrument delivery device. U.S. Pat. No. 4,817,613 describes a coronary guiding catheter. Coronary guiding catheters are used to: (1) conduct interventional catheters into the coronary vasculature and (2) stabilize the proximal aspects of said interventional catheters.

A percutaneous intravascular sheath is another example of a tubular medical instrument delivery device. U.S. Pat. No. 4,874,378 describes a percutaneous intravascular sheath. Percutaneous intravascular sheaths are used to conduct interventional catheters through the tissue planes of the skin and convey said catheters into the confines of the vasculature.

A guidewire channel is an example of a tubular component of a medical device. Guidewire channels are particularly commonplace among devices that are designed for percutaneous introduction. The presence of said channels enables the introduction of said devices over the course of guidewires. This feature enhances the safety and efficiency with which these devices can be advanced within the confines of the body.

An angioscopy catheter is an example of a diagnostic device that contains a guidewire channel. European Patent Application No. EP 0289021 describes a guidewire-directed angioscopy catheter. An atherectomy catheter is another example of a therapeutic device that contains a guidewire channel. U.S. Pat. No. 4,781,186 describes a guidewire-directed atherectomy catheter.

Our invention enables the construction of tubular medical devices and tubular components of medical devices with lower profiles and superior performance characteristics relative to the prior art. The advantages of our invention can be appreciated by reviewing its application to the construction of guiding catheters, percutaneous sheaths and guidewire channels. For clarity, these three applications will be discussed separately. Although the balance of this discussion will focus on these applications, it is understood that the scope of our invention is not limited to the construction of the particular devices described herein.

Guiding Catheters

Cross-sectional area or profile constitutes one of the principle limitations of intravascular guiding catheters of the prior art. The risk associated with the use of guiding catheters of the prior art relates, in part, to the respective profiles of these devices. A well recognized relationship exists between profile and morbidity among intravascular devices in general. Larger profile devices provoke more trauma to the blood vessel wall during introduction within the vascular system, create more resistance during advancement within the vascular system and impair surrounding blood flow to a greater extent, following introduction within the vascular system, relative to lower profile devices.

In addition to these considerations, the profile of super-selective guiding catheters directly impacts the clinical utility of these delivery devices. U.S. Pat. No. 4,581,017 teaches a super-selective guiding catheter. Super-selective guiding catheters deliver interventional devices to remote regions of the vasculature wherein the vessels are commonly small in caliber. The respective profiles of these catheters largely dictate the regions within which said catheters can be advanced.

Considerable effort has been directed toward the development of guiding catheters with progressively lower external profiles. Virtually all of the progress that has been achieved to date has resulted from the development of materials and manufacturing processes that have enabled the construction of these devices with progressively thinner walls. Relatively little benefit has resulted from efforts to modify the fundamental tubular design of these devices which has remained essentially unchanged to date.

The factors that influence the profile of a guiding catheter of the prior art include: (1) the luminal dimensions of the device and (2) the thickness of the walls of the device. The optimal guiding catheter permits independent coaxial mobility of the device contained therein. This feature enables the performance of a device exchange without the need to sacrifice the guiding catheter and hence vascular access in the process. To accommodate this feature, the dimensions of the entire lumen of a guiding catheter of the prior art must exceed the largest profile of the device installed therethrough. Hence, further progress in reducing the profile of guiding catheters of the prior art is constrained by the need to maintain the profile of the entire delivery channel within a range that accommodates the largest profile of the corresponding interventional device installed therethrough.

This relationship pertains to the construction of all delivery catheters of the prior art that afford independent mobility of the interventional device installed therethrough, regardless of the configuration of said interventional device. The delivery of an interventional device of non-uniform profile commonly mandates the use of a prior art guiding catheter that is particularly capacious relative to said interventional device.

Guiding catheters function, in part, to stabilize the proximal aspects of interventional catheters contained therein during the course of interventional procedures. The stability afforded by a guiding catheter varies directly with the thickness of the walls of the shaft of said catheter (provided that similar materials and methods of construction are used in the manufacture of the respective devices). Hence, further progress in reducing the profile of a guiding catheter of the prior art is constrained by the need to maintain the thickness of the shaft walls within a range that confers satisfactory stability to the proximal aspect of the interventional catheter contained therein.

In short, there exists a lower limit to the profile that can be achieved in the construction of a functionally satisfactory guiding catheter of the prior art that permits independent coaxial mobility of the interventional device installed therein. Given this circumstance, alternative delivery systems were developed that enabled the introduction of interventional devices within the confines of the vasculature with lower profiles relative to conventional guiding catheters. For example, U.S. Pat. No. 4,773,413 describes the use of a tubular delivery catheter to convey and stabilize a "ball-tipped" laser catheter within the confines of the vasculature. The tubular element fulfills the function of a guiding catheter. This tubular element is lower in profile than a guiding catheter of suitable luminal profile for use in conjunction with the "ball-tipped" laser by virtue of the fact that the lumen of said tubular element is considerably smaller in profile than the maximal profile of the interventional device contained therein. This configuration enable the construction of a delivery catheter/interventional catheter system of lower profile relative to convention. However, this configuration does not permit separation of the interventional component from the delivery component of the system.

There clearly exists a need for a medical instrument delivery catheter of lower profile relative to prior art guiding catheters of commensurate delivery capacity that permits independent coaxial mobility of the device introduced or withdrawn therethrough.

Guidewire Channels of Medical Devices

One of the principal considerations associated with the construction of a guidewire channel within a diagnostic/interventional device concerns the impact of said channel on the composite profile of said device. As indicated previously, there exists a well-recognized relationship between the profile of a medical device and the morbidity associated with the use of said device.

The impact of a guidewire channel on the composite profile of a guidewire-directed device is particularly evident among systems of the prior art that enable complete separation of the device component from the guidewire component. The ability to completely separate the device component from the guidewire component of a guidewire-directed diagnostic/interventional system enables the exchange of the device without the need to sacrifice intraluminal access during this process. This feature constitutes one of the most fundamental safety features of current generation guidewire-directed interventional medical devices. Typically, separation of the device component from the guidewire component is accomplished by withdrawing the device component over the course of the (extended) guidewire component of the system. To accommodate this feature, given the constraints of the prior art, the dimensions of the entire guidewire channel must exceed the maximal dimensions of the guidewire contained therein. The profile of a guidewire of the prior art is largely dictated by the maximal profile of the guidewire mandrel. Typically, the profile of the mandrel is largest near the proximal end of the guidewire. Because the distal profile of the guidewire channel must accommodate the proximal profile of the guidewire installed therein, separable guidewire-directed systems of the prior art commonly contain guidewire channels and guidewires of uniform profile.

The profile of the proximal aspect of the guidewire mandrel directly impacts the distal profile of the guidewire channel and hence the composite profile of the distal aspect of the system itself. Reducing the profile of the proximal aspect of the guidewire mandrel is constrained by the need to maintain the profile of this segment of the guidewire within a range that confers satisfactory directional control to the system. The directional control of a guidewire-directed diagnostic/interventional system varies directly as a function of the profile of the proximal aspect of the guidewire mandrel contained therein. Hence, further progress in reducing the composite profile of separable guidewire-directed diagnostic/interventional systems is constrained by the need to: (1) maintain the profile of the proximal aspect of the guidewire mandrel within a range that confers satisfactory directional control to the system and (2) maintain the dimensions of the entire guidewire channel within a range that will accommodate the maximal profile of the proximal aspect of the guidewire mandrel contained therein.

Clearly, there exists the need for the design of a guidewire/guidewire-channel system that permits the construction of separable, highly steerable, guidewire-directed diagnostic and therapeutic systems of lower profile relative to the prior art.

Percutaneous Intravascular Sheaths

One of the functional limitations of current generation percutaneous intravascular sheaths concerns the invariability of the luminal dimensions of said delivery devices. As a result of this circumstance, it is frequently necessary to exchange sheaths in the event that a procedure mandates the use of a device of larger profile relative to the luminal dimensions of the sheath. Most notable in this regard is the need to exchange sheaths prior to the performance of an 'ad hoc' angioplasty. The term 'ad hoc' angioplasty refers to the practice of performing an angioplasty immediately following the performance of the diagnostic procedure. This approach to the performance of an angioplasty is becoming increasingly commonplace because it is more efficient and cost-effective relative to the alternative. The performance of an angiogram generally requires the use of a 6-7 French sheath whereas the performance of an angioplasty requires the use of an 8-9 French sheath. The technique required to exchange a low profile sheath for a more capacious sheath commonly provokes blood loss and local trauma to the vasculature. Although it is reasonable to consider installing a large bore sheath at the outset of the angiogram, to circumvent the need to exchange sheaths, this approach exposes patients that are deemed unsuited for intervention, to the added risks associated with the installation of a large bore sheath. Clearly there exists the need for a sheath that can be installed within a relatively small arteriotomy and yet expand, as necessary, to accommodate catheters of progressively larger profile.

SUMMARY OF THE INVENTION

Our invention enables the construction of tubular medical devices and devices containing tubular components or channels that are structurally and/or functionally superior to corresponding devices of the prior art.

For the purpose of this discussion, the term prior art will refer to medical devices containing non-radially expandable tubes, tubular components and/or channels. The use of radially-expandable tubes or channels in the construction of medical devices enables the manufacture of said devices with: (1) lower profiles, (2) greater delivery capacities and (3) greater inter-component mobilities relative to corresponding devices of the prior art.

Our invention enables the construction of the tube, tubular element or channel with a lower profile relative to functionally similar structures that do not expand radially. Our invention thus enables the construction of devices containing radially-expandable components with lower composite profiles relative to corresponding devices of the prior art. Given the inter-relationship between profile and safety, our invention permits the construction of medical devices containing tubes, tubular elements and/or channels that are safer to use compared to the prior art.

Our invention permits the construction of a tube, tubular component or channel that accommodates the passage of a device of larger dimensions than the unexpanded luminal dimensions of the tube, tubular component or channel. Our invention thus permits the construction of tubular instrument delivery devices of greater delivery capacity relative to prior art devices of comparable profile.

Our design enables the construction of multicomponent coaxial devices wherein the central element can be advanced or withdrawn within the confines of a channel contained within the peripheral element that is normally lower in profile relative to the profile of said central element. Hence, our design enables the construction of multi-component tubular medical devices that afford greater inter-component coaxial mobility and versatility relative to corresponding devices of the prior art. Similarly, our design permits the construction of separable multi-component coaxial systems that otherwise would be inseparable. Among other advantages, this latter feature enables the construction of exchangeable devices that otherwise would not permit the performance of an intraoperative exchange without the sacrifice of intraluminal access.

A variety of configurations can be used to construct radially-expandable tubular elements. It is our intent to focus on the advantages inherent to the use of said elements in the construction of medical devices with the understanding that a variety of structures can be used to construct radially-expandable tubular elements.

In summary, the use of radially-expandable tubular elements enables the construction of lower profile, safer, more versatile and more capacious medical devices than the prior art. The use of radially expandable tubular elements further enables the construction of devices that accept the introduction of exchange guidewires that otherwise would not accept the introduction of said wires.

Herein, we describe a radially-expandable tube for use in the construction of tubular medical devices and tubular components of medical devices. It will become evident from the discussion contained herein that the use of a radially-expandable tube enables the construction of tubular medical devices and medical devices containing tubular components with lower profiles and superior performance characteristics relative to the prior art. For brevity, we have focused this discussion on the application of our invention to the construction of medical instrument delivery devices, percutaneous intravascular sheaths and guidewire channels. However, it is understood that the scope of our invention is not limited the these particular applications. The use of a radially-expandable tube in the construction of guiding catheters enables the manufacture of said delivery systems with lower profiles relative to prior art delivery devices of commensurate function and delivery capacity. The use of a radially-expandable tube in the construction of sheaths enables the construction of said delivery devices with adjustable delivery capacity. The use of a radially-expandable tube in the construction of guidewire channels enables the manufacture of highly steerable, separable guidewire-directed interventional devices with lower profiles than heretofore possible.

The foregoing and other aspects of the invention will become evident from the following detailed description of the applications of the invention, illustrations and claims.

BRIEF DESCRIPTION OF THE DRAWINGS

FIGS. 2D–2F illustrate the change in configuration that transpires within the distal aspect of said catheter consequent with the introduction of the device therethrough.

FIGS. 4B–4D are a series of off-center profile views of the device depicted in FIG. 3. These figures illustrate the change in configuration that transpires within the distal shaft and guidewire-channel of the device consequent with the process of withdrawing said device over the course of the guidewire depicted in FIG. 4A.

DESCRIPTION OF THE PREFERRED EMBODIMENTS

Our invention concerns the use of a radially-expandable tubular element in the construction of medical devices containing tubular components and/or channels. In particular, our invention concerns the use of the tubular elements in the construction of device components and channels that function to conduct or convey medical instruments and/or guidewires therethrough. The use of radially expandable tubular elements in the construction of delivery catheters enables their manufacture with lower composite profiles relative to prior art device delivery catheters of comparable delivery capacity. The use of radially expandable guidewire channels in the construction of exchangeable guidewire-directed diagnostic/therapeutic devices enables their manufacture with lower shaft profiles than heretofore possible.

Although our invention applies to the construction of all devices containing tubular components and/or channels that function to conduct or convey devices and/or guidewires therethrough, we will confine our remarks to the use of radially-expandable tubular elements in the construction of a guiding catheter, percutaneous intravascular sheath and guidewire channel, with the understanding that the scope of our invention is not limited to the focus of this discussion.

FIGS. 1A-1D are detailed phantom profile views and two cross-sectional views of an ultra-low profile radially-expandable subselective guiding catheter. The device consists of a shaft, stress riser 27 and proximal adapter 20.

The shaft is composed of three sections 5, 6, and 7 of progressively increasing rigidity. The luminal profile of shaft section 7 is sufficient to accommodate the profile of the largest device intended for delivery therethrough. The corresponding profiles of shaft sections 5 and 6 are considerably smaller. This circumstance enables the construction of shaft sections 5 and 6 with lower external profiles relative to shaft section 7. (See FIGS. 1B and 1D.)

The shaft of the device contains at least two layers; an inner relatively inelastic layer and an outer relatively elastic layer. These are bonded together to provide a delivery channel 15 that is continuous therethrough. The inner layer affords column strength to the shaft. The outer layer functions as a barrier to the flow of fluid and serves to compress the inner layer, thereby reducing the composite profile of the device. Because the outer layer is not required to provide column strength, it can be constructed with particularly thin walls. In the preferred embodiment, a lubricous coating is applied to the outer layer to facilitate the introduction and withdrawal of the device within the confines of the body.

Section 5 is composed of at least two tubular elements; an outer relatively elastic tubular element 14 and an inner relatively inelastic, yet flexible tubular element 11. In one embodiment element 14 comprises a low density polyurethane and element 11 comprises a medium density polyurethane. These two layers are joined distally. Additionally, these two layers are joined longitudinally by means of an eccentric bond 4 (See FIG. 1B), typically provided by heat or an adhesive. Shaft section 6 is similar in configuration to shaft section 5. The rigidity of the respective inner tubular elements, however, is different. The inner tubular element 10, contained within shaft section 6, is more rigid relative to the inner tubular element 11, contained within shaft section 5. Preferably element 10 comprises a high density polyurethane. This difference affords shaft section 6 enhanced rigidity relative to shaft section 5. Inner tubular elements 10 and 11 are joined together at joint 12 (See FIG. 1A), also by heat or an adhesive. Shaft section 7 is composed of three tubular elements; a low density polyurethane outer tubular element 14, a high density polyurethane tubular element 10 and a wire braid tubular element 28 sandwiched therebetween. (See FIG. 1D.) The wire braid tubular element 28 enhances the rigidity of shaft section 7 compared to shaft section 6. This design permits the construction of a shaft that is particularly flexible at the distal end and yet relatively rigid at the proximal end. Our invention further permits the construction of a similar structure wherein the transition in rigidity occurs gradually. We achieve this variable flexibility by a co-tapered extrusion of the inner and outer tubular elements. Variable shaft flexibility affords the device enhanced 'pushability' and guidewire 'trackability' relative to conventional devices containing shafts of uniform rigidity throughout.

Figure 1A:
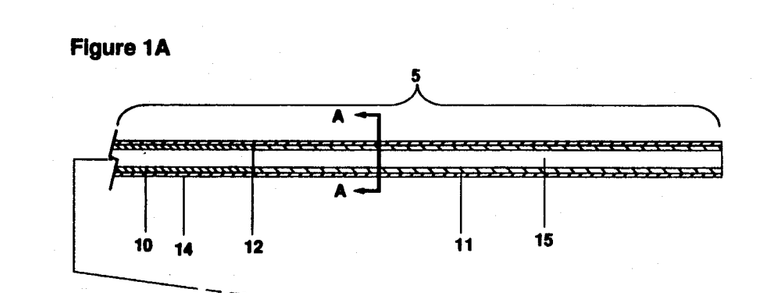
FIGS. 1A–1D are profile and cross-sectional views of a radially-expandable subselective delivery catheter of our design.
Figure 1B:
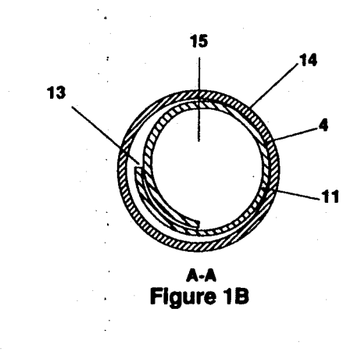
Figures 1C, 1D:
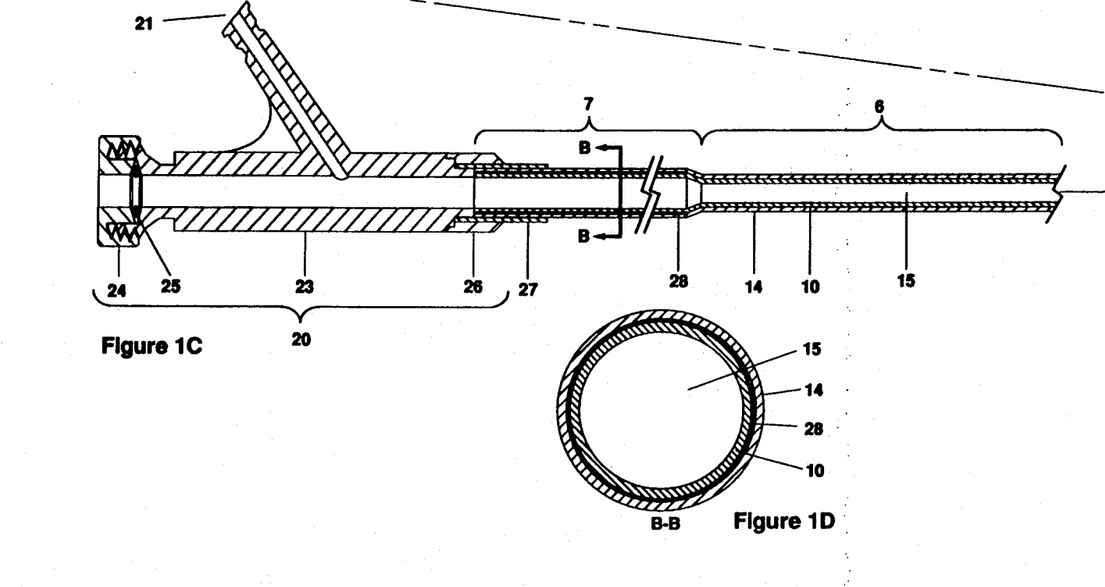

Inner tubular elements 10 and 11 contain a slit 13 that extends the length of shaft sections 5 and 6 and terminates distally to shaft section 7. Slit 13, in conjunction with the elasticity of tubular element 14 enables shaft sections 5 and 6, and the delivery channel 15 contained within these sections, to expand radially in response to the passage of devices of relatively large profile therethrough. This feature enables the shaft of the delivery catheter described herein to accommodate the passage of devices of larger profile than the baseline dimensions of the distal lumen of the catheter. Thus our catheter provides superior device delivery capacity relative to prior art delivery catheters of comparable baseline distal shaft and delivery channel profiles. Correspondingly, this feature enables the construction of our catheter with lower baseline distal delivery channel and shaft profiles compared to prior art guiding catheters of comparable delivery capacity and shaft wall thickness. Given the recognized relationship between device profile and morbidity, our invention enables the construction of a device delivery catheter that is safer to use than prior art catheters of comparable delivery capacity.

In the preferred embodiment, the opposing surfaces of the inner tubular elements, contained within shaft sections 5 and 6, are superimposed upon one another. (See FIG. 1B.) This configuration enables the tubular elements to expand radially within the distal aspect of the catheter and yet remain circumferentially intact, thus precluding the inadvertent escape of a device contained therein through the confines of slit 13. In the preferred embodiment, the distal shaft expands radially in response to the application of minimal outward directed force.

In the preferred embodiment, the tubular elements comprising shaft section 7 are circumferentially bonded together, preferably with heat. The layers comprising shaft sections 5 and 6 are eccentrically bonded together by means of bond 4 that extends longitudinally the length of the shaft sections. The use of an eccentric bond precludes coaxial rotation of the respective tubular elements and yet permits modest inter-component mobility, facilitating radial expansion.

The proximal adapter 20 consists of component 23, side-arm 21, rotator 24, and adjustable O-ring valve 25. (See FIG. 1C.) The interface between component 23 and rotator 24 is a right-hand screw. The O-ring valve 25 is disposed within the lumen of the proximal adapter 20 at the interface between component 23 and rotator 24. This valve allows the distal aspect of the shaft lumen 15 to be sealed and thus preclude the loss of blood therethrough. The function of the O-ring valve 25 can be adjusted by rotation of rotator 24, relative to component 23. Clockwise rotation of rotator 24 relative to element 23 compresses the O-ring, thus closing the valve, whereas counter-clockwise rotation accomplishes the opposite effect. The use of an adjustable valve enables the operator to control blood loss despite the introduction and withdrawal of devices of variable profile therethrough. Side arm 21 provides access to lumen 15 of said device. The infusion of fluid into side arm 21 flushes lumen 15. Side arm 21 is designed to interface with luer-locking components. The proximal adapter is joined to the catheter shaft section 7 by means of a cap 26 and stress riser 27.

The configuration of the catheter tip depends upon the intended use of the device. Clearly, the shaft can be shaped to accept a variety of configurations, including tip configurations that are well known to facilitate negotiation of prior art delivery devices within various regions of the body.

Figure 2A:
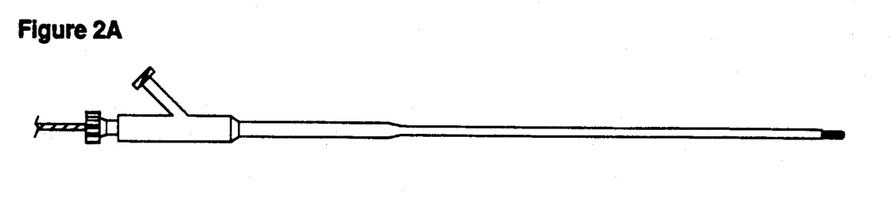
FIGS. 2A–2F are profile views of the catheter depicted in FIG. 1. These figures illustrate the removal of a guidewire from the confines of the catheter and the subsequent introduction of a device, of non-uniform profile, therethrough.
Figure 2B:
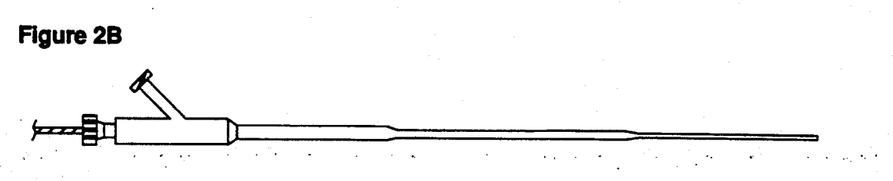
Figure 2C:
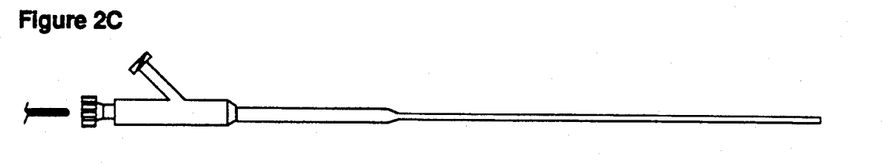
Figure 2D:
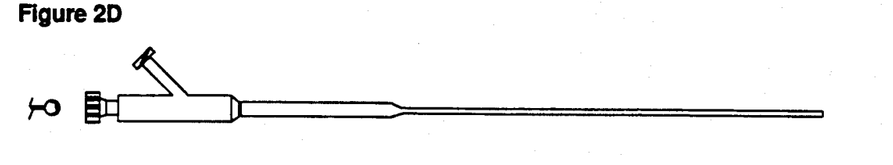
Figure 2E:
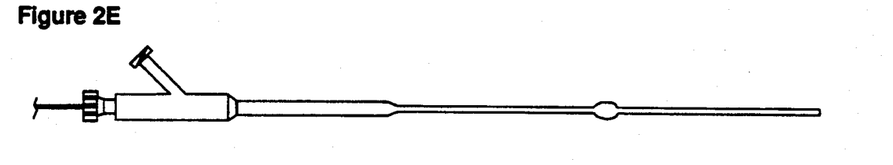
Figure 2F:
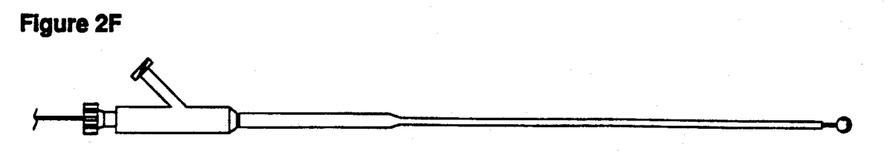

Typically, the device is prepared with a guidewire and advanced within the confines of the body under fluoroscopic control. Rotation of the guidewire enables the operator to steer the device within relatively remote regions. The flexibility of the distal shaft facilitates introduction of the device within regions of the vasculature subserved by particularly tortuous vessels. Once suitably installed, the guidewire can be removed to enable the subsequent introduction of a diagnostic or therapeutic device therethrough. FIGS. 2A-2C illustrate the changes in distal shaft configuration that transpire consequent with the withdrawal therethrough of a guidewire of uniform profile. FIGS. 2D-2F illustrate the changes in distal shaft configuration that transpire consequent with the introduction of a relatively large profile diagnostic/ interventional device of non-uniform dimensions therethrough. An ultrasonic delivery catheter ball-tipped laser catheter (U.S. Pat. No. 4,773,413) is one example of prior art interventional devices of non-uniform dimensions that require introduction within selected regions of the vasculature via guiding catheters.

Prior art guiding catheters contain delivery channels that are uniformly larger in profile relative to the maximal profiles of the devices intended for delivery therethrough. Hence, the delivery of an interventional/ diagnostic device of non-uniform profile via a guiding catheter of the prior art requires the use of a particularly capacious and thus large profile catheter. As evident in FIGS. 2A-2F, the use of radially expandable tubular elements enables the construction of lower profile and hence safer delivery devices than prior art devices of comparable delivery capacity.

The use of radially expandable guidewire channels in the construction of guidewire-directed diagnostic/interventional devices enables the manufacture of these devices with lower composite profiles than prior art devices. FIGS. 3A-3D and 4B-4D illustrate this principle. These figures depict an angioscopy catheter containing a guidewire channel using an embodiment of our invention. FIGS. 3A-3D contain a phantom profile view and two shaft cross-sectional views of the device. The shaft contains a relatively low profile, relatively flexible section 30 and a relatively larger profile, relative inflexible section 31. The shaft is composed of at least two tubular elements, an outer relatively elastic element 36 and an inner relatively inelastic tubular element 38. Two fiber-optic bundles 40 and 41, are imbedded within tubular element 38. (See FIG. 3B.) These bundles function respectively to conduct light in an antegrade direction and return an image in the retrograde direction. These fiber-optic bundles exit the confines of the device via side arm 46. The guidewire channel 34, contained within shaft section 30 is radially expandable by virtue of slit 44 and the elasticity of tubular element 36. Slit 44 extends longitudinally the length of shaft section 30 and terminates distal to shaft section 31. The guidewire channel 34 contained within shaft section 31 is sufficiently large in profile to accommodate the largest profile segment of the guidewire intended for introduction or withdrawal therethrough and it does not permit radial expansion.

Figure 3A:
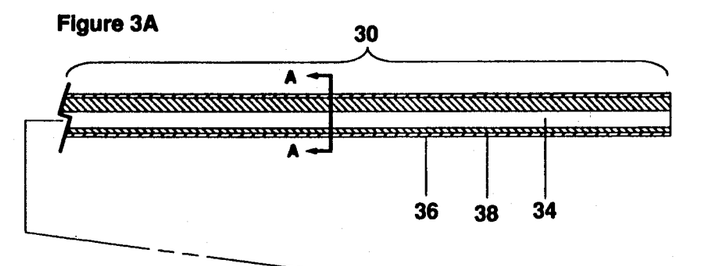
FIGS. 3A–3D are a simplified profile view and two cross-sectional views of a guidewire-directed angioscopy catheter that contains a radially-expandable guidewire channel of our design.
Figure 3B:
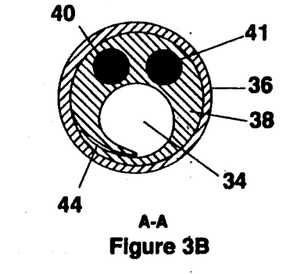
Figures 3C, 3D:
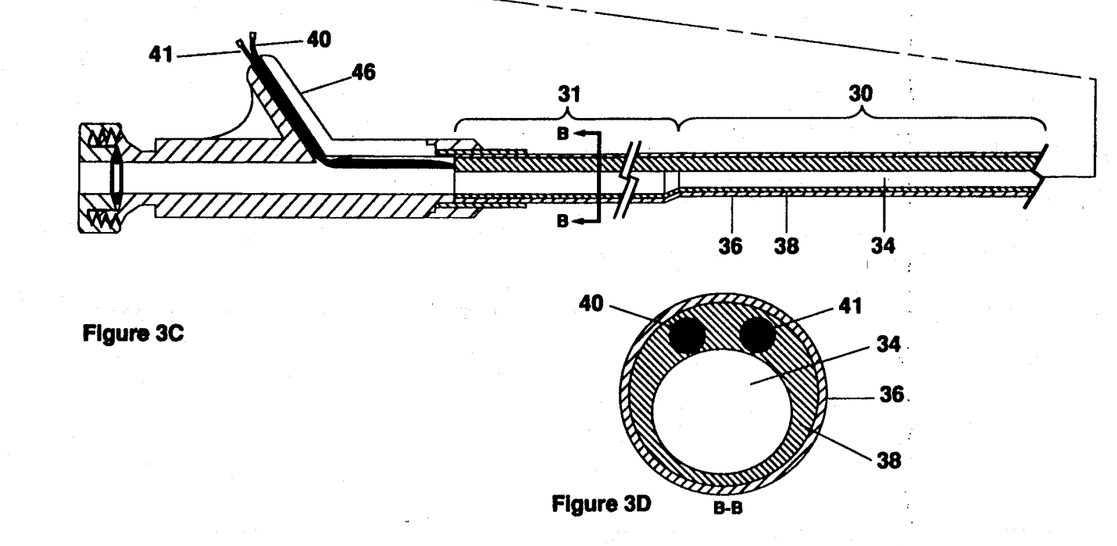
Figure 3E:
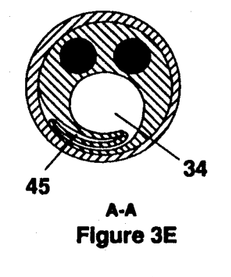
FIG. 3E is a cross-sectional view of the catheter shown in FIG. 3C for another embodiment. For the embodiment depicted in FIG. 3E, the inner member has a folded or wrapped configuration, as opposed to the configuration shown in FIG. 3B.

FIG. 3E is a cross section of the section 30 illustrating an alternative embodiment of the invention. For the embodiment depicted in FIG. 3B, a slit was employed to allow radial expansion. For the embodiment depicted in FIG. 3E, the inner tubular element 38 includes a section 45 which is contiguous, but which has been folded in the overlapped configuration shown. In this manner, as channel 34 is expanded, that portion 45 of the inner element will unfold as necessary.

Because the guidewire lumen within the distal aspect of this device is radially expandable, the device can be constructed to conform to the surface of a guidewire of non-uniform profile and yet accommodate the introduction and withdrawal of said guidewire therethrough. Hence, the use of this device, in conjunction with a guidewire component containing a low profile segment that extends through the distal confines of the catheter component, provides a lower composite profile than functionally comparable guidewire-directed systems of the prior art that are designed to accommodate guidewires of uniform profile throughout.

Reducing the profile of the guidewire channel of a prior art device, with the intent to reduce the composite profile of the device, is constrained by the need to maintain the dimensions of the guidewire channel sufficiently large to accommodate the largest profile segment of the guidewire disposed proximal to this region. Stated differently, reducing the profile of the distal guidewire channel obligates reducing the profile of the proximal aspect of the guidewire mandrel. Any departure from this basic principle precludes the ability to separate the guidewire component from the catheter component of the device intraoperatively. Reducing the profile of the mandrel invariably compromises the directional control of the composite device. Hence, further progress in reducing the profile of guidewire-directed diagnostic/therapeutic devices of the prior art, that afford independent catheter-guidewire coaxial mobility, is constrained by the need to: (1) maintain the proximal profile of the guidewire mandrel within a range that confers satisfactory directional control to the system and (2) maintain the corresponding profile of the distal guidewire channel sufficiently large to accommodate the proximal profile of said guidewire mandrel, thus enabling withdrawal of the catheter component from the guidewire component of the system.

A guidewire of non-uniform profile, containing a low profile region, can be constructed that is functionally comparable to prior art stand alone guidewires of uniform profile throughout. This circumstance obtains because: (1) the mandrel components are largely responsible for the function of prior art guidewires and (2) prior art guidewires of uniform profile contain progressively tapered mandrels with low profile distal segments. The wire coil components of stand alone guidewires of the prior art: (1) afford flexibility to the distal aspect of the guidewire that extends beyond the region of the mandrel and (2) render the device uniform in profile. In effect, the coil disposed proximal to the end of the mandrel, in the case of prior art stand alone guidewires, functions largely to enhance the profile of the tapered segment of the mandrel and affords no significant advantage to the wire in terms of directional control (i.e., rotational torque delivery potential). Hence, this coil can be removed, exposing the tapered mandrel contained therein, enabling the construction of a guidewire of non-uniform profile, that contains a low profile distal segment and yet provides comparable directional control relative to prior art guidewires of uniform profile.

Figure 4A:
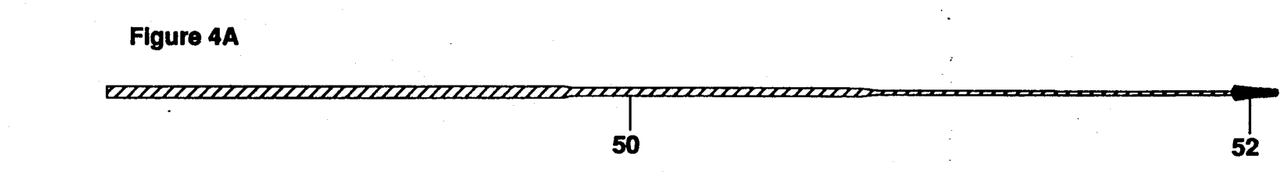
FIG. 4A is an enlarged profile view of a "stand alone" guidewire of non-uniform profile.
Figure 4B:
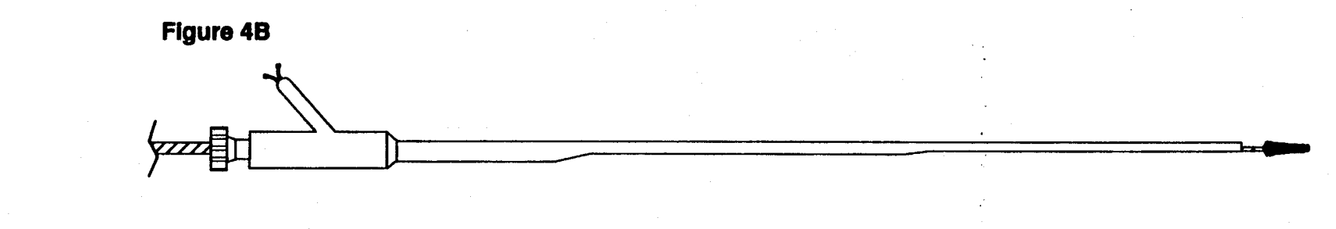
Figure 4C:
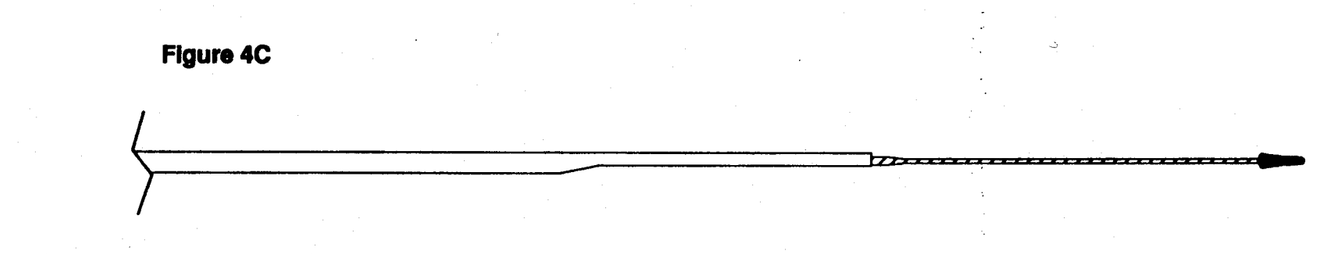
Figure 4D:
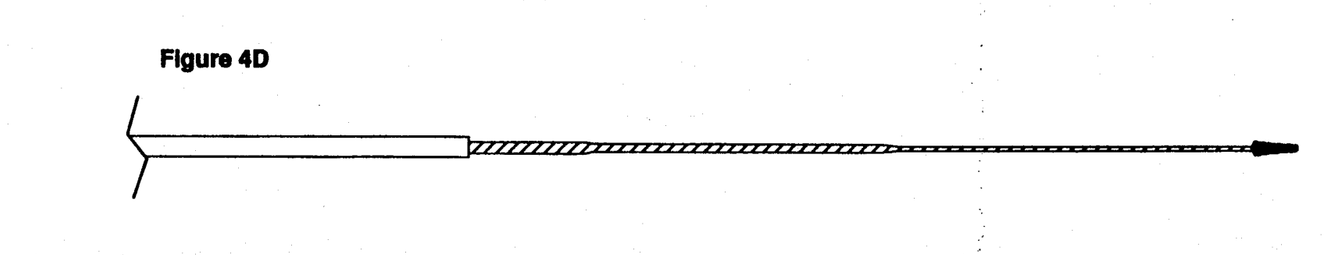

FIG. 4A is an enlarged profile view of such a guidewire of our design. The guidewire contains a progressively tapered mandrel 50, a flat wire ribbon (not shown) and a radiopaque tip coil 52. The radiopaque tip coil 52 extends over the distal aspect of mandrel 50. The wire ribbon (not shown) extends throughout the length of the interior of the tip coil 52. The tip coil 52 is joined proximally to mandrel 50 and to the flat wire ribbon. Distally, the tip coil is joined to the flat wire ribbon. The use of a guidewire of this configuration, in conjunction with a diagnostic/therapeutic catheter containing a radially expandable guidewire channel that is designed to conform to the surface configuration of said guidewire, enables the construction of a guidewire-directed assembly with comparable steerability and coaxial guidewire mobility relative to the prior art. It further enables the assembly to have a lower composite profile than functionally comparable devices of the prior art. FIGS. 4B-4D are a series of profile views of the angioscopy catheter illustrated in FIGS. 3A-3D. These figures illustrate the changes in shaft and guidewire channel configuration that transpire consequent with the withdrawal of the angioscopy catheter over the guidewire illustrated in FIG. 4A. Given the recognized relationship between device profile and safety, the use of a radially expandable guidewire channel in conjunction with a guidewire of non-uniform profile, containing at least one low profile distal segment, enables the construction of a highly steerably system that is lower in distal profile and thereby safer to use than functionally comparable devices of the prior art. Although we describe the use of our guidewire/guidewire channel system in conjunction with an angioscopy catheter, it should be understood that our system has application to all guidewire-directed exchangeable interventional/diagnostic systems and that the use of our system in their construction enables their manufacture with lower composite profiles than heretofore possible.

Figures 5A, 5B:
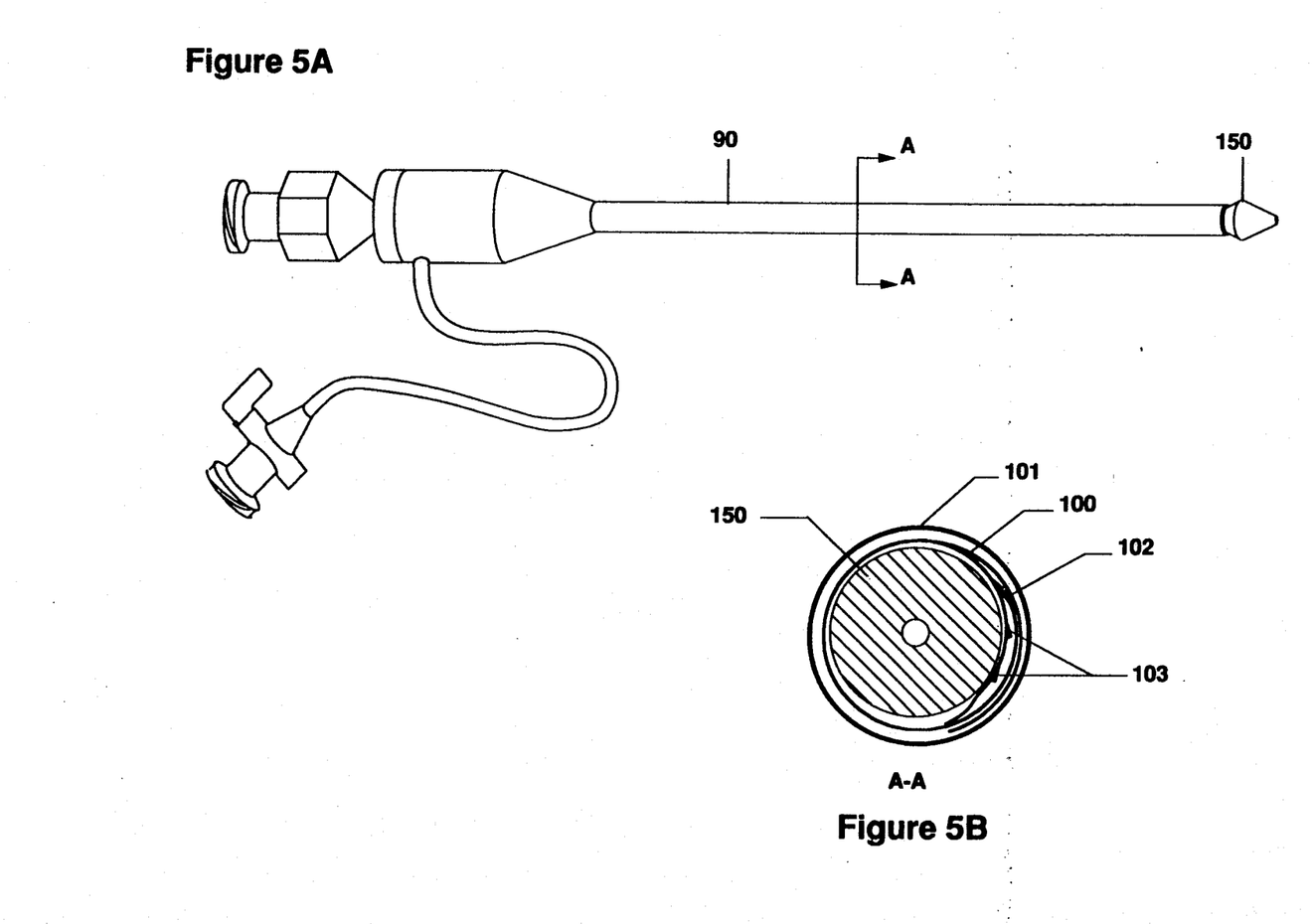
FIGS. 5A and 5B is an off-center profile view and enlarged detailed mid-shaft cross-sectional view of a radially-expandable side arm sheath and dilator assembly.
Figure 6A:
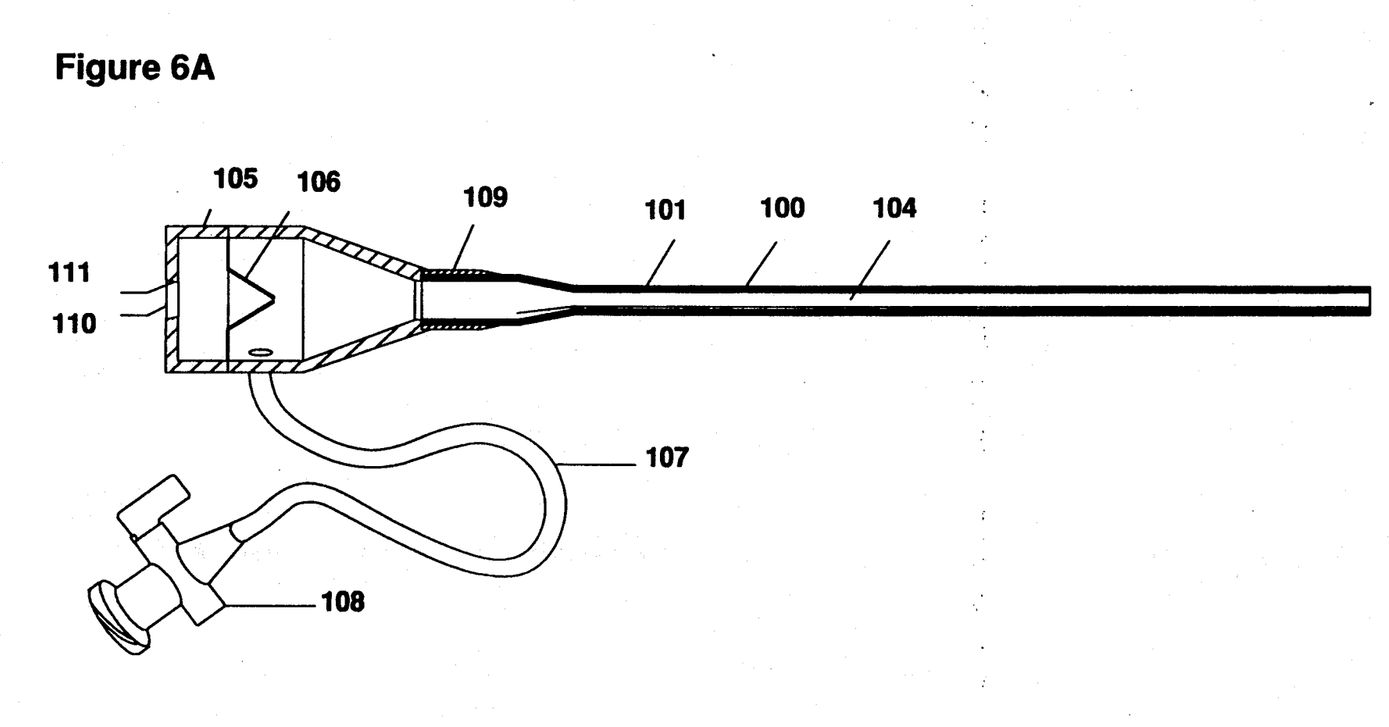
FIGS. 6A–6C are profile views of the sheath component and two dilator components.
Figure 6B:
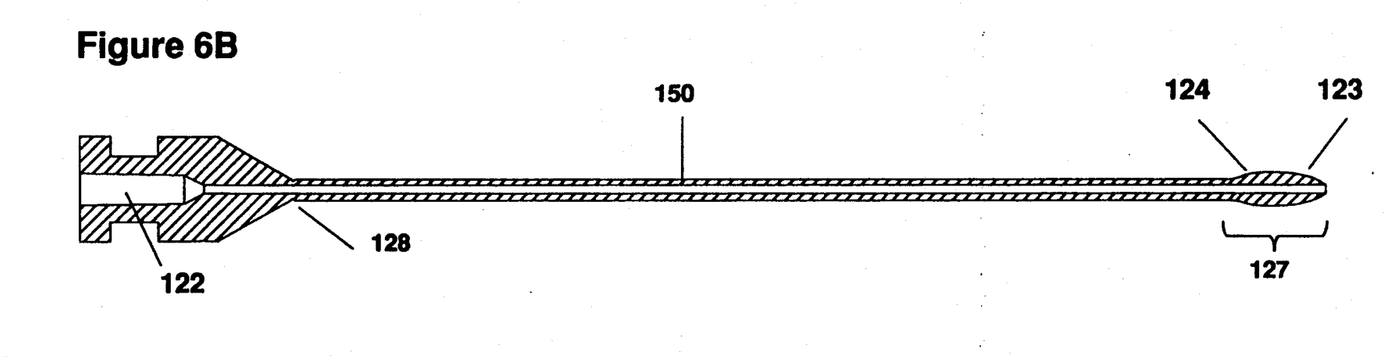
Figure 6C:
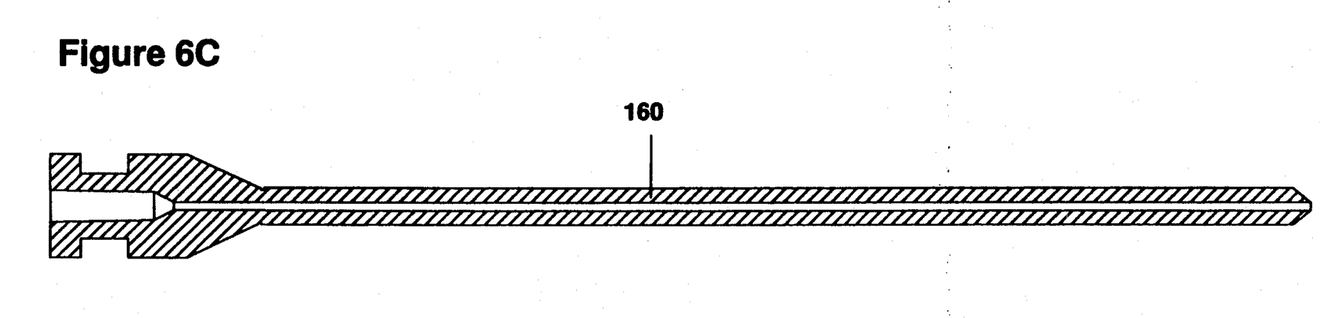

In addition to the aforementioned applications, the use of radially expandable tubular elements can be applied to the construction of intravascular sheaths. FIG. 5A is a profile view of a side-arm guidewire-directed intravascular sheath and dilator assembly that contains a radially expandable shaft of our design. FIG. 5B contains an enlarged mid-shaft cross-sectional view of same. FIG. 6A is a longitudinal cross-sectional view of the side arm sheath 90. FIGS. 6B and 6C are corresponding views of two guidewire-directed dilators 150, 160 intended for use with the sheath.

The sheath assembly consists of a side arm sheath 90 and one or more dilators 150, 160. The sheath consists of a shaft and a proximal hub. The shaft is composed of an inner tubular element 100 and an outer tubular element 101. A relatively rigid material, for example polypropylene, is preferable for the construction of inner tubular element 100. Conversely, a thermoplastic elastomer is preferable for the construction of outer tubular element 101. The inner tubular element 100 is designed to accommodate positive radial expansion over a specific range of radial dimensions. This is accomplished by constructing the element with overlapping surfaces and disposing at their interface a ratcheting mechanism consisting of a series of longitudinally disposed teeth 103 and a latch 102. The passage of a device therethrough of larger profile than the baseline luminal profile of the shaft engages latch 102 with successive teeth 103 and thereby radially expands the shaft of the sheath and maintains the shaft in its expanded configuration.

The outer tubular element 101 is bonded eccentrically to the inner tubular element 100 forming an interior lumen 104. This outer tubular element: (1) prevents the passage of fluid through the walls of the shaft and (2) compresses the inner tubular element 100 and thereby maintain the desired degree of expansion of said element. Because the outer tubular element 101 is not required to provide column strength to the shaft, it can be constructed with particularly thin walls. The external surface of outer component 101 is preferably coated with a lubricous substance to facilitate the introduction of the device within the confines of the body.

The proximal hub contains a side-arm 107 and hemostatic valve 106. The side arm terminates with a stopcock 108 designed to interface with luer-locking components. The lumen of said side-arm is continuous with the lumen of the sheath. The infusion of fluid into the side-arm functions to flush the contents of the sheath. The hub consists of a body 105 which contains a one-way multi-leaved valve 106. Valve 106 functions to accommodate the passage of devices introduced therethrough and yet prevent the exit of blood and/or bodily fluids therefrom. The port 110 at the proximal end of the proximal hub is coaxial to the center of valve 106 and channel 104 and functions to expedite the introduction of devices therethrough. A strain relief 109 extends across the interface between the hub and shaft. The leading edge of said strain relief is tapered.

Typically, the sheath is prepared with the dilator 150 illustrated in FIG. 6B and this assembly is introduced over a guidewire within the confines of the vasculature. The dilator 150 contains a guidewire channel 122 and provides: (1) increased column strength to the sheath during introduction within the body, (2) a wedge shaped leading edge to the assembly and (3) a means of dilating the sheath to a suitable channel profile following introduction of the sheath within the confines of the vasculature. The dilator 150 is formed of a rigid material. Proximally, it contains a groove 128 that is designed to interface with taper 111 contained in port 110 of the sheath. This tongue and groove configuration functions to couple the two assembly components together during the process of introducing the sheath within the confines of the vasculature and yet permit separation of said components following introduction of said sheath therein. Distally, the dilator 150 contains a bulbous region 127. This bulbous region is defined by a leading taper 123 and expansion taper 124. The sheath and dilator are designed such that the distal end of the sheath is proximal to the bulbous region 127 of said dilator.

This sheath/dilator assembly configuration affords numerous advantages over prior art assemblies containing radially non-expandable shafts. This configuration enables the introduction of the assembly through a lower profile arteriotomy or venotomy than the prior art because our device is designed to be introduced in a radially contracted state and to expand radially subsequent to insertion. The maximal profile of the bulbous region 127 of dilator 150 corresponds to the intended channel profile of the device. Introduction of the sheath assembly is accomplished in the conventional manner. Withdrawal of the dilator, however, through the confines of the sheath, increases the profile of the delivery channel to the desired profile as bulbous region 127 is withdrawn through the shaft. As with the above-described devices, this feature enables the insertion of our assembly with decreased morbidity relative to prior art devices of similar device delivery capacity. Our device further can be reconfigured to accept progressively larger profile devices simply by installing dilators of progressively larger cross-sectional profiles therethrough. FIG. 6C is a profile view of such a dilator. This feature enables the insertion of an intra-aortic counter-pulsation balloon catheter or angioplasty guiding catheter through the confines of a baseline low profile sheath that otherwise could not be used to convey these devices. This feature circumvents the need to exchange sheaths to enable the introduction of such devices, among others, following the performance of an angiography. Angiography is commonly performed, prior to the performance of an angioplasty or the insertion of an intra-aortic balloon pump. Angiography can be accomplished with the use of a 6 French sheath whereas the performance of an angioplasty and intra-aortic counter-pulsation requires the use of substantially larger sheaths. This circumstance currently mandates exchanging sheaths, a process that invariably provokes local trauma to the vasculature and blood loss. Our sheath permits the performance of both procedures without the need to exchange the sheath in the interim and circumvents the need to install a large bore sheath at the outset to accomplish this end.

In summary, our invention concerns the use of radially-expandable tubular elements in the manufacture of medical devices and components of medical devices that conduct or convey devices and/or guidewires therethrough. The use of our invention enables the construction of guiding catheters of lower profile and superior delivery capacity than prior art devices. The use of our tubular elements enables the construction of percutaneous sheaths with lower profiles and superior functional versatility than prior art devices. The use of our tubular elements in the construction of guidewire channels for guidewire-directed diagnostic/therapeutic systems enables the construction of assemblies with lower composite profiles and comparable directional control and inter-component coaxial mobility than functionally comparable systems of the prior art. Given the relationship between device profile and morbidity, the use of radially-expandable tubular elements enables the construction of medical devices containing tubes and/or channels that are safer to use than prior art devices.

We claim:

1. A composite tube for an intravascular medical device, the composite tube capable of conveying an object of a first cross-sectional profile therethrough, the composite tube comprising:
    an outer tube having a first elasticity and radially expandable between a first position and a second position, the first position having a second cross-sectional profile smaller than the first cross-sectional profile, the second position having a third cross-sectional profile larger than the first cross-sectional profile; and
    an inner member disposed inside the outer tube and extending longitudinally through the outer tube, the inner member having a second elasticity less than the first elasticity and defining a coaxially self-supporting channel, the inner member formed to include a sheet of material having a first edge and a second edge slidably overlapped in a rolled configuration forming a slit between the first edge and the second edge; said outer tube being circumferentially continuous and fluid-impermeable and extending the full length of said inner tube.

2. A composite tube as in claim 1 wherein:
    the outer tube is relatively flexible possessing a first column strength; and
    the inner member is relatively inflexible possessing a second column strength the second column strength being greater than the first column strength.

3. A composite tube as in claim 1 wherein:
    the inner member and the outer tube extend over a first length; and
    the inner member is divided into at least two portions, a first portion having a first rigidity and a second portion having a second rigidity.

4. A composite tube of claim 1 having a proximal end and a distal end, the distal end being more flexible than the proximal end.

5. A composite tube for an intravascular medical device, the composite tube comprising:
    an inner layer including a rolled sheet of material with a first elasticity, the rolled sheet having a first longitudinal edge and a second longitudinal edge overlapping to form a circumferentially coexisting junction wherein said first longitudinal edge and said second longitudinal edge are circumferentially slidable relative to each other to allow radial expansion and contraction of the rolled sheet of material; and
    an outer tube of material having a second elasticity, the second elasticity greater than the first elasticity, the outer tube bonded to the inner layer between said first longitudinal edge and said second longitudinal edge wherein the cross-sectional profile of the outer tube is selected to elastically constrict the radial displacement of said first longitudinal edge and said second longitudinal edge; said outer tube being circumferentially continuous and fluid-impermeable and extending the full length of said inner layer.

6. A composite tube as in claim 5 wherein the inner layer is constructed to provide coaxial support to the composite tube.

7. A composite tube of claim 5 further comprising a proximal end and a distal end wherein the distal end has a greater flexibility than the proximal end.

8. A composite tube as in claim 5 wherein the inner layer defines a radially expandable tube having a proximal end and a distal end, wherein said proximal end has a first rigidity and said distal end has a second rigidity and said first rigidity and said second rigidity are unequal.

9. The composite tube of claim 5 further comprising a fiber optic bundle disposed longitudinally in said inner layer.

10. A composite tube for an intravascular medical device, the composite tube comprising:
    an outer tube having a first radial elasticity; and
    an inner layer disposed within said outer tube, the inner layer formed from a sheet of relatively unpliant material wrapped into the configuration of a tube wherein an inside surface of said sheet and an outside surface of said sheet circumferentially overlap along a sliding junction, said inner layer longitudinally bonded to said outer tube and radially expandable therein; said outer tube being circumferentially continuous and fluid-impermeable and extending the full length of said inner layer.

11. A composite tube for conveying a medical device therethrough, the composite tube comprising:

a first section having an outer tube of a first rigidity, a first resiliency and defining a shaft, an inner layer disposed within the outer tube, the inner layer formed of a sheet of material of a second rigidity and a second resiliency and rolled into a generally tubular configuration with an inside surface and an outside surface generally overlapping, wherein the outer tube has a first cross-sectional profile in the natural assembled condition and permits radial expansion upon conveyance of a device having a second, larger cross-sectional profile through said inner layer forcing said inner layer to expand radially and communicating radial forces upon said outer tube as said overlapping edges slide relative to each other; said outer tube being circumferentially continuous and fluid-impermeable and extending the full length of said inner layer.

12. The composite tube of claim 10 further comprising a fiber optic bundle disposed longitudinally in said inner layer.

* * * * *